United States Patent [19]

Alvarado

[11] Patent Number: 4,904,268
[45] Date of Patent: Feb. 27, 1990

[54] PROSTHETIC DEVICE

[76] Inventor: Alfredo Alvarado, 4310 Bayview Dr., Ft. Lauderdale, Fla. 33308

[21] Appl. No.: 242,827

[22] Filed: Sep. 12, 1988

[51] Int. Cl.[4] .......................... A61F 2/36; A61F 2/30; A61F 2/32
[52] U.S. Cl. ........................................ 623/23; 623/18; 623/22
[58] Field of Search .......................................... 623/23

[56] References Cited

U.S. PATENT DOCUMENTS 3,658,056  4/1972  Huggler et al. ........................ 623/26
4,693,724  9/1987  Rhenter et al. ........................ 623/23

FOREIGN PATENT DOCUMENTS 0274094  7/1988  European Pat. Off. .............. 623/23

OTHER PUBLICATIONS

"BIAS" Hip Prosthesis shown on attached page listing patent numbers 4,546,501, 3,605,123 and 3,813,699.

Primary Examiner—Richard J. Apley
Assistant Examiner—Stephanie L. Iantorno
Attorney, Agent, or Firm—Oltman and Flynn

[57] ABSTRACT

A hip prosthesis comprising a hollow intramedullary stem with a tapered, closed inner end for insertion along the medulla of the femur, a brace segment on the outer end of the stem for engaging the stump of the femoral neck, a spherical ball on the brace segment, and a lag screw for slidable insertion through a passage in the brace segment into the screw-threaded interior of the stem. The stem has longitudinal slots through which the screw teeth of the lag screw project to engage cancellous bone.

4 Claims, 1 Drawing Sheet

U.S. Patent  Feb. 27, 1990  4,904,268
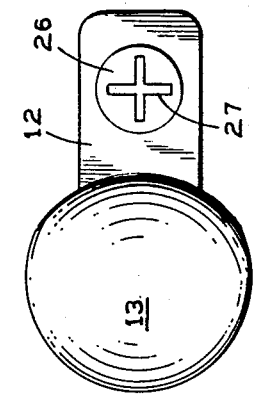
FIG. 2
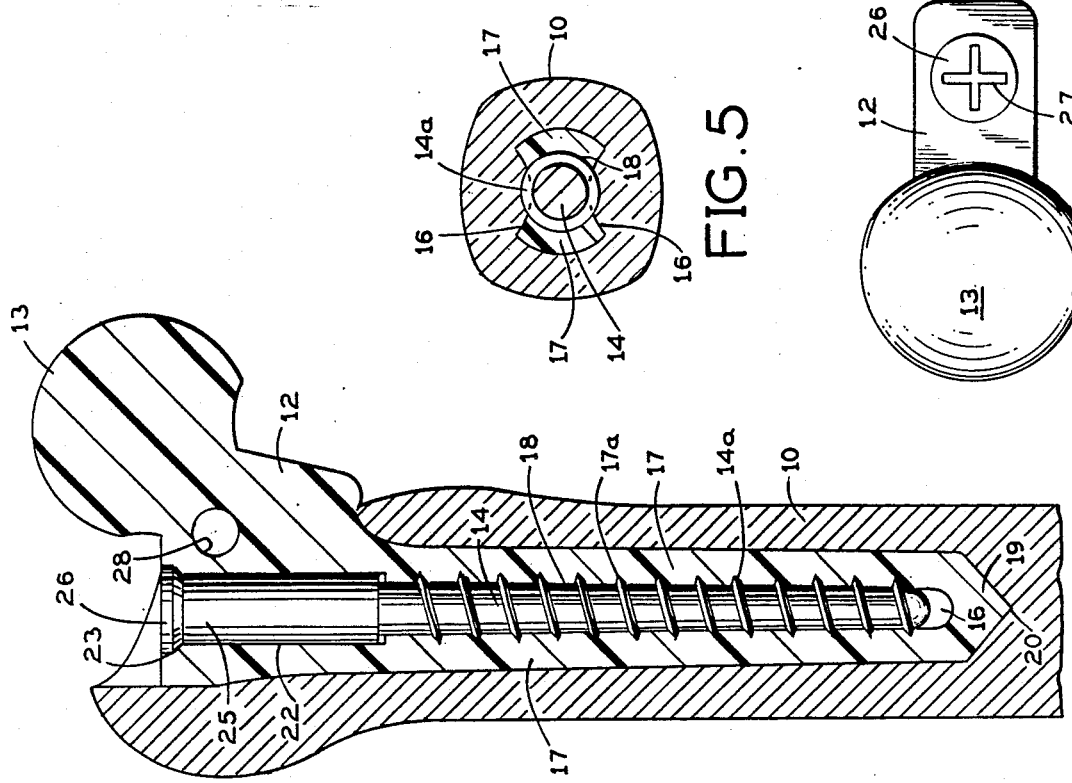
FIG. 5
FIG. 4
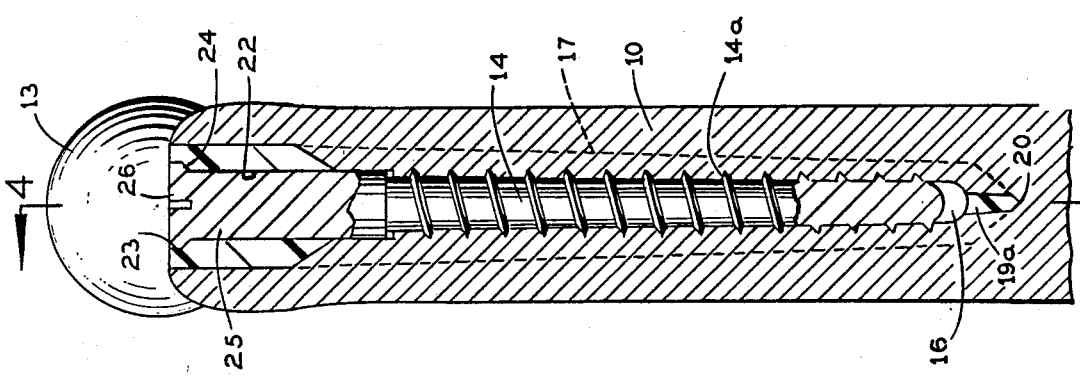
FIG. 3
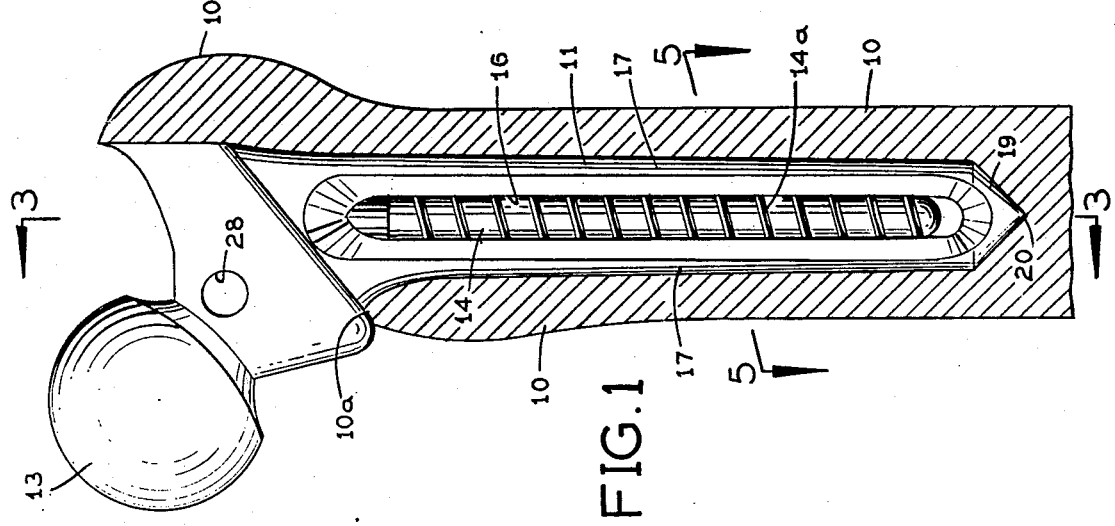
FIG. 1

PROSTHETIC DEVICE

SUMMARY OF THE INVENTION

This invention relates to an implantable prosthetic device for restoring normal function to a fractured or diseased bone, such as the femur.

Various implanted prosthetic devices are in use at present to repair damaged bones. In many distances problems are encountered to secure a strong and lasting mechanical connection between the prosthesis and the bone. The principal cause of these failures is believed to be the repetitively changing stresses within the prosthesis and the bone. The use of bonding cements, such as methyl-methacrylate, may improve the stability of the prosthesis for a limited period of time. However, in many cases loosening of the mechanical connection is experienced as a result of stress of the loss of structural integrity of the cement. In addition to this, poor design of the prosthesis, by not recognizing fully the effects of stresses caused by dynamic loads, may lead to failure.

A principal object of this invention is to provide a novel prosthetic device for implantation in a person's damaged bone.

Another object of this invention is to provide such a device which will remain anchored in the bone despite changing stresses, such as those caused by dynamic loads on the bone.

Preferably, the prosthetic device of the present invention comprises a screw with sharp-edged teeth, such as a lag screw, an elongated slotted stem which is inserted into the medulla of the bone, and a brace segment on the outer end of the stem for engaging the end of the bone to distribute stresses. The stem has longitudinal slots and arcuate side segments between these slots which are internally screw-threaded to receive the teeth of the screw, which also project out through these slots for engagement in the cancellous bone around the medulla. The brace segment has a passage therein which registers with the longitudinal recess in the stem between its arcuate side segments for the insertion of the screw.

In the case of a hip prosthesis, a spherical ball is joined to the brace segment on one side of its passage.

Further objects and advantages of this invention will be apparent from the following detailed description of a presently preferred embodiment which is illustrated schematically in the accompanying drawings.

DESCRIPTION OF THE DRAWING

FIG. 1 shows in elevation a prosthetic device for a person's hip, the femur of which, with the head removed, is shown in section;

FIG. 2 is a top plan view of this device;

FIG. 3 is a longitudinal section taken along the line 3—3 in FIG. 1;

FIG. 4, is a similar view taken along the line 4—4 in FIG. 3; and

FIG. 5 is a cross-section taken along the inclined section line 5—5 in FIG. 1.

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

In the drawing, reference numeral 10 designates a person's femur from which the femoral head has been removed because of a break or disease. To repair a hip in this condition, a prosthetic device in accordance with the presently-preferred embodiment of this invention comprises:

an elongated, slotted, hollow stem 11 for insertion into the bone 10 along its medulla a brace segment 12 joined integrally to the outer end of the stem and engageable with the outer end 10a of what remains of the femur;

a generally spherical head 13 joined integrally to the outer end of brace segment 12 and located to one side of stem 11;

and a lag screw 14 extending through brace segment 12 and screw threadedly received in stem 11.

The slotted stem 11 has two identical, diametrically opposed, longitudinal slots 16 (FIGS. 1 and 5) which are separated by arcuate side segments 17 of the stem. The slots 16 open into a central longitudinal recess 18 in the stem (FIGS. 4 and 5) between the side segments 17 of the stem. The side segments are internally screw-threaded, as shown at 17a in FIG. 4. As shown in FIG. 5, each of the slots 16 is wider circumferentially of the stem than each of its arcuate side segments 17, so the slots provide relatively wide openings into the central recess 18 along most of the length of stem 11. The central recess 18 and the longitudinal slots 16 end at a closed inner end segment 19 of the stem 11 (FIGS. 1 and 4) which tapers to a sharp point 20. This inner end segment 19 has a central web 19a, as shown in FIG. 3, along the axis of the central recess 18 in the stem.

The lag screw 14 is received in the longitudinal recess 18 in the slotted stem 11 for almost the entire length of that recess. The lag screw for most of its length has a shank of solid cylindrical cross-section with sharp-edged external screw threads 14a that threadedly engage the internal screw threads 17a on the inside of the arcuate side segments 17 of the slotted stem 11.

The brace segment 12 has a cylindrical passage 22 which extends into slotted stem 11 and opens into the longitudinal recess 18 in the stem. Passage 22 and recess 18 are coaxial. The diameter of passage 22 is large enough to slidably receive the threads of lag screw 14. At the outer end of brace segment 12 a cylindrical counterbore 23 opens into passage 22 at a frusto-conical seat 24. The lag screw 14 has an enlarged cylindrical shank segment 25, which has a sliding fit in the passage 22, and an enlarged head 26 on its outer end which is shaped complementary to the counterbore 23 and the frusto-conical seat 24 in the brace segment 12. This head engages seat 24 to limit the extent to which the lag screw 14 can be screwed into the slotted stem 11. As shown in FIG. 2, the head 26 of the lag screw has a Phillips head screw-driver slot 27. As shown in FIGS. 1 and 3, the slots 16' in stem 11 extend into the passage 22 through the brace segment 12 where the inner end of the cylindrical shank segment 25 of screw 14 is located. Consequently, as shown in FIG. 1, the screw-threaded shank 14 of the screw is exposed along its entire length at the slots 16 in the opposite sides of stem 11 for engagement in the cancellous bone (FIGS. 32 and 5).

The ball-shaped, generally spherical head 13 of the prosthetic device is joined to the brace segment 12 on one side of its passage 22 and it extends outwardly from brace segment 12 completely to one side of the slotted stem 11.

As shown in FIGS. 1 and 4, on the side of stem 11 where the generally spherical head 13 is located, the brace segment engages the outer end face 10a of the stump 10' of the femoral neck laterally beyond the slotted stem 11.

Also, on this side of the stem 11, the brace segment has a cross-hole 28 for receiving a screw driver or other tool to facilitate removing the slotted stem 11 from the bone 10, when desired.

The first step in inserting the present prosthetic device into a damage bone 10 is to drill a pilot hole in the bone along its medulla.

The next step is to drive the slotted stem 11 into the medulla along this pilot hole until the brace segment 12 on its outer end engages the outer face 10a of the damaged bone. The tapered, closed inner end of the stem pilots the stem through the cancellous bone within the femur 10, seeking the medullar center of the bone.

After the slotted stem 11 has been fully inserted, the lag screw 14 is inserted slidably through the passage 22 in brace segment 12 and into the longitudinal recess 18 in the slotted stem 11 between its internally screw-threaded side segments 17 until the head 26 of the screw seats on the frusto-conical seat 24 in the brace segment. The sharp-edged screw threads 14a of the lag screw project through the longitudinal slots 16 in stem 11 and finally engage in the cancellous bone, as shown in FIGS. 3 and 5, to anchor the lag screw 14 and the slotted stem 11 in the cancellous bone. The unitary combination of the lag screw 14, the slotted stem 11 and the brace segment 12 insures that forces applied to the artificial head 13 will be properly distributed without unfavorable stress concentration because of the large areas of interface between the natural bone and this prosthetic device.

While the invention has been disclosed with reference to a hip prosthesis, it should be understood that with appropriate structural modification it may be applied to other damaged bone or skeletal joints.

I claim:

1. A prosthetic device for implantation in a person's femur having the femoral head removed, leaving the stump of the femoral neck exposed, comprising:
    a screw having an enlarged head on one end, a substantially cylindrical shank segment joined at one end to said head, and a shank with sharp-edged screw teeth thereon extending from the opposite end of said substantially cylindrical shank segment;
    a body having an elongated slotted stem with a closed, tapered, inner end of insertion into the femoral neck along the medulla, said body having an opposite outer end away from said inner end of the slotted stem, said body at said outer end thereof having a brace segment joined to said slotted stem and projecting laterally beyond said stem on one side to engage the stump of the femoral neck, said brace segment having a passage therethrough with an enlarged counterbone which is open at the outer end of said body, said stem having a longitudinal recess therein registering with said passage through said brace segment and extending to said closed, tapered, inner end of the stem, said stem for a substantial part of its length having circumferential arcuate side segments partially bordering said longitudinal recess and diametrically opposed surfaces between said side segments, said surfaces defining substantially parallel longitudinal planes, each of said surfaces having concave longitudinal slots formed therein which open into said longitudinal recess, said side segments being internally screw-threaded and screw-threadedly engaged by portions of said teeth of the screw while the remainder of said teeth project out through said longitudinal slots in the stem for engagement in the cancellous bone around the medulla without projecting beyond said parallel longitudinal planes, said passage through the brace segment being shaped and dimensioned to slidably pass said shank of the screw with said screw teeth thereon, said substantially cylindrical segment of the screw being slidably received in said passage through the brace segment, and said head on the screw being seated in said counterbore.

2. A prosthetic device according to claim 1 wherein said slots in the stem open into said passage through the brace segment, and said screw-threaded shank is exposed along its entire length at said slots in the stem.

3. A prosthetic device according to claim 1 wherein said closed inner end of the slotted stem is tapered to a sharp point.

4. A prosthetic device according to claim 3 and further comprising a generally spherical head joined to said brace segment at one side of said passage through the brace segment, said head extending outward from said brace segment substantially completely to one side of said slotted stem, and said brace segment having a cross-hole therein between said passage through the brace segment and said head.

* * * * *